US00PP13659P29

(12) United States Plant Patent
Zerr

(10) Patent No.: US PP13,659 P2
(45) Date of Patent: Mar. 18, 2003

(54) POINSETTIA PLANT NAMED 'FISPUE WHITE'

(75) Inventor: Katharina Zerr, Simmern (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/099,764

(22) Filed: Jun. 19, 1998

(51) Int. Cl.[7] ..... A01H 5/00
(52) U.S. Cl. ..... Plt./304
(58) Field of Search ..... Plt./304, 305

(56) References Cited

U.S. PATENT DOCUMENTS

PP7,755 P * 12/1991 Hrebeniuk ..... Plt./304
PP8,772 P * 6/1994 Jacobsen ..... Plt./304
PP9,726 P * 12/1996 Dummen ..... Plt./304
PP9,878 P * 4/1997 Jacobsen ..... Plt./304

OTHER PUBLICATIONS

GTITM UPOVROM Citation For 'Fispue White' as per CA PBR 96–974; Dec. 16, 1996.*
GTITM UPOVROM Citation For 'Fispue White' as per DE PBR EUP 00197; Jan. 20, 1997.*
GTITM UPOVROM Citation For 'Fispue White' as per JP PBR 9738; Mar. 31, 1997.*
GTITM UPOVROM Citation For 'Fispue White' as per QZ PBR 980031; Jan. 8, 1998.*
GTITM UPOVROM Citation For 'Fispue White' as per IL PBR 02874; Feb. 8, 1998.*

* cited by examiner

*Primary Examiner*—Howard J. Locker
*Assistant Examiner*—Kent L. Bell
(74) *Attorney, Agent, or Firm*—Foley & Lardner

(57) ABSTRACT

The cultivar 'Fispue White' is characterized by uniform cream-white bract color; ovate bracts which are slightly folded forming a horizontally or somewhat upward-directed inflorescence with almost no gaps in the arrangement of the bracts around the cluster of cyathia; intensely green foliage and leaves almost without any lobes; medium-tall, relatively compact and well-branched plant habit; and relatively good rooting characteristics.

1 Drawing Sheet

BACKGROUND OF THE INVENTION

The present invention relates to a new and distinct cultivar of Poinsettia plant known by the cultivar name 'Fispue White', and botanically known as *Euphorbia pulcherrima.*

'Fispue White' is a naturally occurring whole plant mutation of 'Fispue', (U.S. Plant Pat. No. 9,315). 'Fispue' is a cultivar characterized by light pink bracts with white margins, medium-green foliage, and medium tall plant habit.

The mutation was discovered by the inventor Katharina Zerr among a group of flowering pot plants of the parent cultivar in Hillsheid, Germany, in December 1994.

Two plants had developed white bracts, and one of these, which was completely mutated, was used for vegetative propagation which was carried out in Hillscheid, Germany by the inventor. In the spring of 1995, cuttings from this plant were planted and the resulting plants were checked for stability.

'Fispue White' was compared to other white clones and varieties in a first small trial cultivation in late autumn 1995, and again, on a larger scale, in autumn 1996. Horticultural examination initiated in 1995 and continuing thereafter has demonstrated that the combination of characteristics as herein disclosed for 'Fispue White' are firmly fixed and are retained through successive generations of asexual reproduction.

BRIEF DESCRIPTION OF THE INVENTION

The following traits have been repeatedly observed and are determined to be basic characteristics of 'Fispue White' which in combination distinguish this poinsettia as a new and distinct cultivar:

1. Uniform cream-white bract color;
2. Ovate bracts which are slightly folded forming a horizontally or somewhat upward-directed inflorescence with almost no gaps in the arrangement of the bracts around the cluster of cyathia;
3. Intensely green foliage and leaves almost without any lobes;
4. Medium-tall, relatively compact and well-branched plant habit;
5. Medium to early flowering response; and
6. Relatively good rooting characteristics.

'Fispue White' has not been observed under all possible environmental conditions. The phenotype may vary significantly with variations in environment such as temperature, light intensity, and daylength without, however, any variance in genotype. The following observations, measurements and comparisons describe plants grown in Langley, British Columbia, Canada, under greenhouse conditions which approximate those generally used in commercial practice.

Of the many commercial cultivars known to the inventor, the most similar in comparison to 'Fispue White' is the parent variety 'Fispue', and the variety 'Peterstar White' (U.S. Plant Pat. No. 9,878).

In comparison to the pink and white-colored variety 'Fispue', 'Fispue White' has completely white colored bracts with stems, petioles and veins that are without traces of anthocyanin.

In a side by side comparison with 'Peterstar White', 'Fispue White' has a slightly taller (up to 5 cm) and more uniformly shaped plant habit. The bracts of 'Fispue White' are more smooth (less rugose) and less distinctly folded. Sufficiently colored bracts are developed somewhat earlier so that 'Fispue White' can be marketed about one week earlier than 'White Peterstar'.

This application is co-pending with U.S. Plant patent application Ser. No. 09/099,768 which is drawn to the cultivar 'Fispue Silver'. A brief comparison between 'Fispue White' and 'Fispue Silver' is shown in Table A.

TABLE A

| | 'FISPUE WHITE' | 'FISPUE SILVER' |
|---|---|---|
| Foliage color | Uniform medium-green, RHS 137A | Generally lighter green, RHS 138A-B, with lighter green spots and white margin |
| Size/growth | Medium tall, moderately vigorous growth | Low to medium tall, relatively slow growing |
| Height | 31 cm | 24.5 cm |
| Beginning of flowering | Mid-season | Medium to late (10 weeks), about 10 days later than 'Fispue White' |
| Shape of bracts | Somewhat rugose surface, almost no lobing, entire margin, ovate | Somewhat rugose surface, slightly lobed, partly crenated or irregular margin, ovate |
| Shape of leaves | Smooth surface, with or without weak lobes, entire margin, broad ovate | Surface slightly rugose, slightly lobed, margin with irregular crenation, ovate to broad elliptical |

BRIEF DESCRIPTION OF THE DRAWING

The accompanying color photographic sheet shows typical inflorescences and foliage of 'Fispue White' with colors being as true as possible with an illustration of this type. The photograph is a side view of a typical mature potted plant.

DETAILED BOTANICAL DESCRIPTION

In the following description, color references are made to The Royal Horticultural Society Colour Chart, the color values were determined indoors in a north light. The plants described were grown in a greenhouse in Langley, British Columbia, Canada, in autumn 1997. Rooted cuttings were planted into 15 cm pots on August 1, and were pinched 18 days later. The minimum temperature was 23° C. in early August, 20° C. from late August to November 15, and 16° C. until the plants were finished.

The plants developed flowers under natural short-day conditions. Observations and measurements were taken at the beginning of flowering.

Classification:

*Botanical.*—*Euphorbia pulcherrima.*

*Commercial.*—'Fispue White'.

Parentage: Naturally occurring mutation of 'Fispue'.

Plant description:

*Form.*—Shrub, self-branching, producing a medium to high number of branches.

*Growth habit.*—Medium tall, and moderately compact habit; height (above soil) is 31 cm; average number of branches is 9.2.

*Rooting.*—Medium, about 24 days.

*Blooming habit.*—Beginning of flowering under natural short day conditions in autumn; botanically, in late November; commercially (bracts sufficiently colored), in late November.

*Flowering response time.*—About 8.5 weeks.

*Foliage.*—Shape: Broad ovate, without or with only weak lobes, most often with slightly rounded base, and with acuminate tip. Texture: Smooth, weak veins. Margin: Entire. Size: Leaf blade length is 13.3 cm; leaf blade width is 8.5 cm; petiole length is 4.5 cm. Color: Medium green with light green veining; upper surface is R.H.S. 137A; under surface is R.H.S. 138A. Leaf Petiole: Light green with no anthocyanin.

Flowering description:

*Inflorescence.*—Consists of slightly folded and somewhat upward directed and slightly reflexed bracts with a tight center.

*Average number of inflorescences.*—7.2; under favorable conditions, approximately 80% of the branches develop a complete inflorescence.

*Average diameter of inflorescence.*—29.8 cm.

*Bracts, Shape.*—Ovate, without or with only very weak lobes, rounded base and acuminate tip, flat.

*Texture.*—Surface somewhat rugose and slightly folded.

*Color.*—Cream white; upper surface is about R.H.S. 4D; lower surface is about R.H.S. 150D.

*Size.*—Largest bract length is 16.25 cm (including petiole); width is 9.5 cm.

*Number.*—Approximately 6–8 true bracts at the beginning of flowering with 3–4 completely colored transient bracts.

*Postproduction longevity.*—Mature bracts do not change color; under strong light and long-day conditions, only the youngest, immature bracts change color and turn fresh green at the tip after about 3 weeks.

*Petiole.*—1–2 cm in length, whitish green.

*Cyathia.*—A medium number (about 8–10) in a narrow cluster; medium to light green, top whitish; medium sized, good retention.

*Diameter of cyathia cluster.*—22.0 mm.

*Nectar cups.*—Medium sized, golden yellow, with no anthocyanin.

Reproductive organs:

*Stamens.*—Filaments whitish to yellowish; infertile, abortive.

*Pistils.*—Style light green to white stigma whitish.

*Ovaries.*—Triangular; 3-celled; 3 ovules.

*Disease resistance.*—Typical of the species.

I claim:

1. A new and distinct poinsettia plant named 'Fispue White', as illustrated and described.

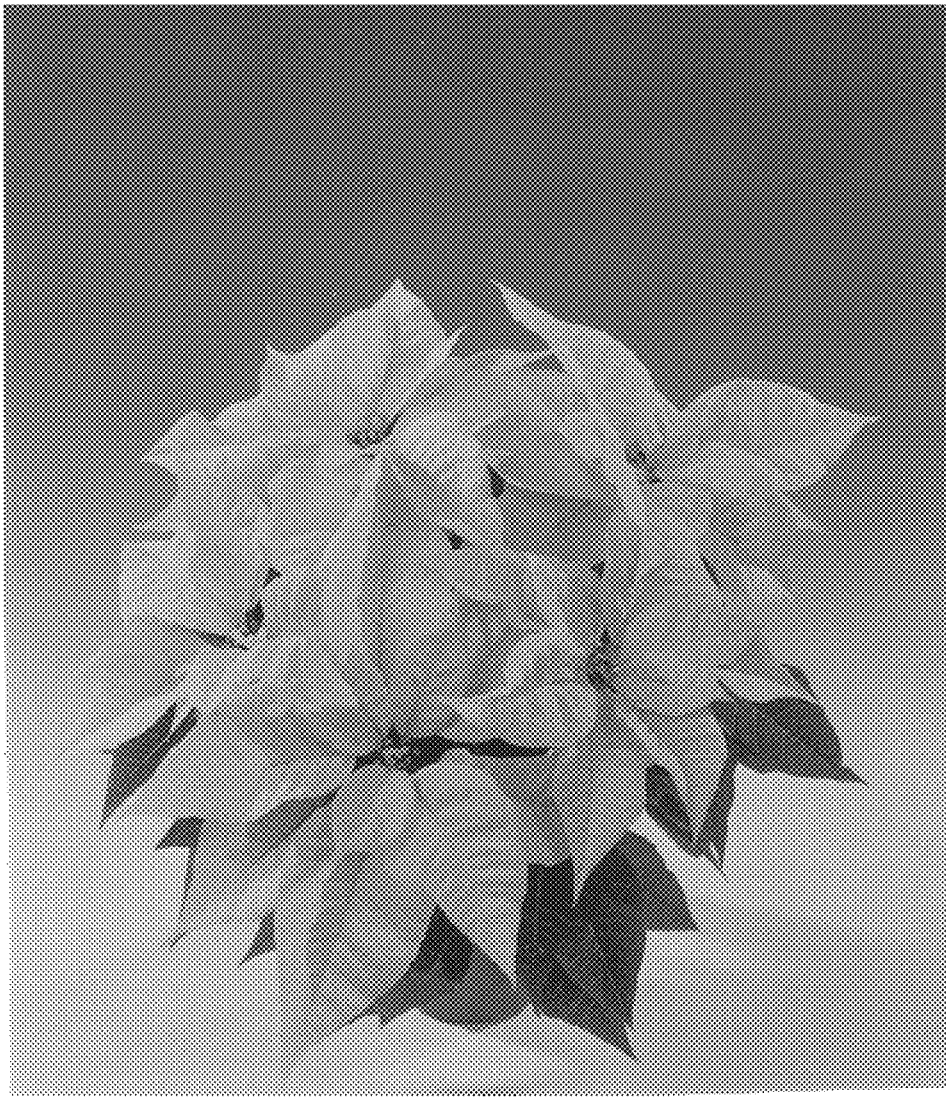

* * * * *